(12) United States Patent
Wilhelm et al.

(10) Patent No.: US 8,580,300 B2
(45) Date of Patent: Nov. 12, 2013

(54) PHARMACEUTICAL FORMULATION FOR TREATING THE UPPER DIGESTIVE TRACT

(75) Inventors: Rudolf Wilhelm, Bischweier (DE); Pröls Markus, Freiburg/Breisgau (DE)

(73) Assignee: Dr. Falk Pharma GmbH, Freiburg (DE)

( * ) Notice: Subject to any disclaimer, the term of this patent is extended or adjusted under 35 U.S.C. 154(b) by 322 days.

(21) Appl. No.: 13/054,844

(22) PCT Filed: Jul. 2, 2009

(86) PCT No.: PCT/EP2009/058320
§ 371 (c)(1), (2), (4) Date: Jan. 19, 2011

(87) PCT Pub. No.: WO2010/009961
PCT Pub. Date: Jan. 28, 2010

(65) Prior Publication Data
US 2011/0123460 A1    May 26, 2011

(30) Foreign Application Priority Data
Jul. 21, 2008   (EP) ..................................... 08013091

(51) Int. Cl.
*A61K 9/20* (2006.01)
*A61K 9/46* (2006.01)
*A61K 31/56* (2006.01)
*A61K 31/58* (2006.01)

(52) U.S. Cl.
USPC ........... 424/466; 424/464; 514/174; 514/181; 514/182

(58) Field of Classification Search
USPC ................... 424/464, 466; 514/174, 181, 182
See application file for complete search history.

(56) References Cited

U.S. PATENT DOCUMENTS

| 5,607,697 A | * | 3/1997 | Alkire et al. ................... 424/495 |
| 5,639,475 A | * | 6/1997 | Bettman et al. ................ 424/466 |
| 5,709,886 A | * | 1/1998 | Bettman et al. ................ 424/495 |
| 5,807,577 A | * | 9/1998 | Ouali ............................ 424/466 |
| 5,807,578 A | * | 9/1998 | Acosta-Cuello et al. ...... 424/466 |
| 2006/0013873 A1 | | 1/2006 | Yang et al. |
| 2007/0191323 A1 | * | 8/2007 | Hill et al. ....................... 514/171 |
| 2008/0187586 A1 | * | 8/2008 | Skrtic et al. .................... 424/468 |

FOREIGN PATENT DOCUMENTS

EP      0 720 473 B      11/1998
WO     WO 03/080023     * 10/2003

OTHER PUBLICATIONS

Elad, et al., "Budesonide: A Novel Treatment for Oral Chronic Graft Versus Host Disease," Oral Surgery Oral Medicine Oral Pathology Oral Radiology and Endontics, vol. 95 (3), pp. 308-311 (2003).
Spencer, et al., "Budesonide: A Review of its Pharmacological Properties and Therapeutic Efficacy in Inflammatory Bowel Disease," Drugs, ADIS International Ltd., vol. 50 (5), pp. 854-872 (1995).

* cited by examiner

*Primary Examiner* — James H. Alstrum-Acevedo
(74) *Attorney, Agent, or Firm* — Chalin A. Smith; Smith Patent Consulting

(57) ABSTRACT

The invention relates to an effervescent tablet for preparing a mouth rinsing solution, wherein the effervescent tablet exhibits a high release rate of budesonide. A high availability of the active ingredient during use as a mouth rinsing solution on the inflamed mucosa of the upper digestive tract is thereby achieved. The advantage of the formulation according to the invention lies in the bioavailability comparable to oral forms of administration, which allows the formulation to be used safely over an extended period of time.

12 Claims, 2 Drawing Sheets

Fig. 1: Quantity of budesonide released in water from different effervescent tablet formulations and from gastric juice-resistant capsules, ground up by pestle and mortar, compared to pure active ingredient solubility ive pharma-
ceutical active
PHARMACEUTICAL FORMULATION FOR TREATING THE UPPER DIGESTIVE TRACT

PRIORITY

This application corresponds to the national phase of International Application No. PCT/EP2009/058320 filed Jul. 2, 2009, which, in turn, claims priority to European Patent Application No. 08.013091.7 filed Jul. 21, 2008, the contents of which are incorporated by reference herein in their entirety.

FIELD OF THE INVENTION

The present invention relates to a pharmaceutical formulation, namely an effervescent tablet, for treating the upper digestive tract, which comprises as pharmaceutical active ingredient budesonide or a pharmaceutically acceptable salt or derivative thereof.

BACKGROUND OF THE INVENTION

Pharmaceutical formulations which contain budesonide and are for oral administration with controlled release in the intestinal tract are known from EP-A-0 720 473.

These formulations have been used for a relatively long time in the treatment of intestinal diseases, such as Crohn's disease, are effective (Bar-Meir, Gastroenterology, 1998, p. 835-840) and have an improved safety profile (Andus, Digestive Diseases and Sciences, 1 Feb. 2003, p. 373-378).

The use of glucocorticoids, in particular budesonide, is generally known for the treatment of diseases which are associated with inflammation processes. These diseases also include those of the oral cavity, the pharynx and the oesophagus. The active ingredient budesonide has been used successfully, for example in GVHD (graft versus host disease) (Elad et al., Oral Surg. Oral Med. Oral Pathol. and Radial Endod. 2003, 95, p. 308-311).

WO03/06629 describes lozenges containing an active ingredient core which is sheathed by a water-soluble polysaccharide (gellan gum). The active ingredient is inside the core and not intermixed with the sheath. Glucocorticoids, for example budesonide are mentioned as possible active ingredients. The tablet is suitable for buccal use.

For treating inflammatory processes in the oral cavity, the preparation of a drug form is desired which is reproducible as a ready-for-use formulation, releases sufficiently high concentrations of active ingredient at the inflammation site and exhibits a local effect.

The direct use of the active ingredient following the grinding up by pestle and mortar of capsules resistant to gastric juice to treat GVHD (Elad, 2003) is known. This direct use of the active ingredient mentioned in the prior art suffers from various disadvantages, for example of not being a ready-for-use, industrially producible formulation with a reproducible dosage. Grinding up tablets also has the disadvantage that uniform high concentrations of active ingredient are not provided at the inflammation site.

The specific tablet formulation is used for buccal administration, in particular with the objective of absorbing an active ingredient buccally into the systemic circulation. Wetting the entire region of the oral cavity with dissolved active ingredient for local use is not possible.

The high instability of budesonide in dissolved form rules out the production of a dissolved pharmaceutical preparation containing budesonide. Over an extended period of time, such a budesonide solution would not be stable without a precise pH adjustment and the addition of preservatives and further stabilisers.

An object of the present invention is to provide a pharmaceutical formulation which can be administered orally and which no longer suffers from the mentioned disadvantages.

Therefore, according to the invention, a formulation is provided which exhibits a rapid, improved solubility for budesonide when prepared as a mouth rinsing solution, results in a high local concentration of active ingredient and furthermore allows a safe use with few side effects over an extended period of time. In addition, the effervescent tablet according to the invention allows stable storage and simple handling.

SUMMARY OF THE INVENTION

It has been found that a specifically prepared mouth rinsing solution, produced from an effervescent tablet, is particularly suitable for the treatment. Unlike a tablet, such a mouth rinsing solution can be used in equal measure in the entire oral cavity as well as in the pharynx and in the oesophagus, since the active ingredient is present in high quantities in dissolved form. The effervescent tablet also affords significant advantages with regard to long-time stability of the drug form up until use and a simple and accurate dosage.

Likewise, an effervescent tablet affords significant advantages in respect of the stability of the administration form after opening.

The effervescent tablet according to the invention for the preparation of a mouth rinsing solution which can be administered orally contains budesonide. The IUPAC name of budesonide is 16,17-(butylidenebis(oxy))-11,21-dihydroxy-(11-β,16-α)-pregna-1,4-diene-3,20-dione. In a preferred embodiment, each effervescent tablet contains from 0.1 to 10 mg of budesonide. Particularly preferably, budesonide is present in a quantity of from 1 mg to 5 mg and most particularly preferably in a quantity of approximately 3 mg per effervescent tablet.

The budesonide used in the effervescent tablet must satisfy the quality and purity requirements imposed on a pharmaceutical preparation. Micronised budesonide is preferably used. The size of the budesonide particles plays an essential part in the dissolution rate and the resorbability. Budesonide is preferably used in which the particle size distribution is adjusted such that at least 90% of the particles have a diameter of less than 20 μm, preferably less than 10 μm. In a particularly preferred embodiment, 100% of the particles have a diameter of less than 10 μm, 95% of the particles have a diameter of less than 5 μm and 80% of the particles have a diameter of less than 3 μm. The particle diameter is determined by conventional measuring methods.

To increase the solubility of budesonide in the mouth rinsing solution prepared from the effervescent tablet according to the invention, the effervescent tablet according to the invention preferably contains polyvinylpyrrolidone in a concentration of from 0.5 to 10% by weight, more preferably in a quantity of between 1.0 and 3.0% by weight, in each case based on the total weight of the prepared effervescent tablet.

Polyvinylpyrrolidone is a polymerisation product of vinylpyrrolidone. A number of fractions with different molecular sizes or molecular chain lengths are commercially available. The molecular mass spectrum ranges from 10,000 to 350,000. Polyvinylpyrrolidone with a molecular size of between approximately 15,000 and 150,000 is preferably used. A particular characteristic of polyvinylpyrrolidones is the good solubility both in water and in polar organic solvents, such as alcohols or glycerine.

Furthermore, the effervescent tablet according to the invention preferably contains another solubiliser or emulsifier, namely docusate sodium (sodium dioctylsulphosuccinate) in a concentration of from 0.1% to 5%, preferably from 0.2% to 2.0%, the quantities relating to the weight of the prepared effervescent tablet.

In a most particularly preferred embodiment, the effervescent tablet according to the invention contains both polyvinylpyrrolidone and docusate sodium.

So that the effervescent tablet according to the invention dissolves effectively following contact with water, it contains an effervescent mixture comprising a pharmaceutically acceptable acid in solid form and a compound containing carbonate and/or hydrogen carbonate.

In the effervescent tablet according to the invention, the pharmaceutically acceptable acid used is such an acid which is available in solid form, does not pose any health threats and does not produce an unpleasant taste. The acid which is preferably used is citric acid. The effervescent mixture also contains a compound which contains carbonate and/or hydrogen carbonate and which releases carbon dioxide upon contact with acid, as a result of which the effervescent tablet dissolves. This is preferably sodium carbonate or sodium hydrogen carbonate.

In a preferred embodiment, the effervescent tablet according to the invention also contains an agent which produces a cooling effect in the mouth. In a preferred embodiment, this is butanamide (N-2,3-trimethyl-2-isopropylbutanamide). This agent is preferably used in a quantity of from 0.1 to 1.0, particularly preferably in a quantity of between 0.3 and 0.8% by weight, based on the prepared effervescent tablet.

The effervescent tablet according to the invention is preferably used for the production of a medicament to prepare a mouth rinsing solution which can be administered orally, to treat inflammatory changes in the upper digestive tract.

When used, the effervescent tablet is dissolved in a specific quantity of a liquid, preferably water, the quantity of water required to dissolve the effervescent tablet amounting to between 5 and 20 ml, preferably between 5 and 15 ml and particularly preferably approximately 10 ml of water.

The inflammatory changes of the upper digestive tract treated by the mouth rinsing solution which can be prepared by the effervescent tablet are preferably inflammatory changes of the digestive tract in the region of the oral cavity and/or pharynx. In a usual method of application, the mouth rinsing solution is produced by dissolving the effervescent tablet in water and then the user gargles with this mouth rinsing solution for a predetermined time which can be between 2 and 15 minutes, preferably approximately 10 minutes, and rinses his mouth. Thereafter, the user does not swallow the mouth rinsing solution, but spits it out.

The inflammatory changes of the upper digestive tract are preferably not infectious inflammations. They can have different causes, for example radiotherapy, organ transplantation and/or chemotherapy. In a preferred embodiment, the inflammatory changes of the upper digestive tract are mucositis, an autoimmune disorder of the oral cavity, Crohn's disease in the upper digestive tract and eosinophilic oesophagitis.

DETAILED DESCRIPTION OF THE PREFERRED EMBODIMENTS

Preferred embodiments of the present invention are illustrated by the following examples.

Example 1

Surprisingly, it was found that the solubility of budesonide effervescent tablets is significantly increased by the addition of polyvinylpyrrolidone (PVP) and ducosate sodium. The composition of different effervescent tablets is shown in Table 1. The composition designated GO397X414 was investigated in more depth and proved to be particularly suitable in the later experiments.

The following Table 1 summarises the formulations of the tested effervescent tablets. The composition varies only in the components Povidone K25 (polyvinylpyrrolidone) and docusate sodium which were varied to improve the solubility of budesonide. Slight differences in the individual formulations were compensated by mannitol.

TABLE 1

Composition of the effervescent tablet formulations
Composition [mg]

Step 1: Granulation

| | | | | | | |
|---|---|---|---|---|---|---|
| Budesonide | 3 | 3 | 3 | 3 | 3 | 3 |
| Sodiumdihydrogencitrate | 67 | 67 | 67 | 67 | 67 | 67 |
| Disodiumhydrogencitrate | 15 | 15 | 15 | 15 | 15 | 15 |
| Sodiumhydrogencarbonate | 45 | 45 | 45 | 45 | 45 | 45 |
| Povidone K25 (PVP) | 2 | 2 | — | — | 4 | 4 |

TABLE 1-continued

Composition of the effervescent tablet formulations
Composition [mg]

| | | | | | | |
|---|---|---|---|---|---|---|
| Docusate-sodium | 0.05 | — | 0.05 | — | — | — |
| Aspartam | 1 | 1 | 1 | 1 | 1 | 1 |
| Granules | 133.05 | 133 | 131.05 | 131 | 135 | 135 |
| Step 2: Final mixture | | | | | | |
| Povidone K25 (PVP) | — | — | — | — | — | 3 |
| Mannitol | 5.95 | 6 | 7.95 | 8 | 4 | 4 |
| Macrogol 6000 | 5 | 5 | 5 | 5 | 5 | 5 |
| Butanamide[1] | 0.9 | 0.9 | 0.9 | 0.9 | 0.9 | 0.9 |
| Magnesium-stearate | 0.1 | 0.1 | 0.1 | 0.1 | 0.1 | 0.1 |
| Final mixture | 145 | 145 | 145 | 145 | 145 | 148 |
| Effervescent tablet (Code) | G0397X414 | G0397X415 | G0397X416 | G0397X417 | G0397X418 | G0397X419 |

[1]Chemical name: N-2,3-trimethyl-2-isopropylbutanamide

Figure 1:
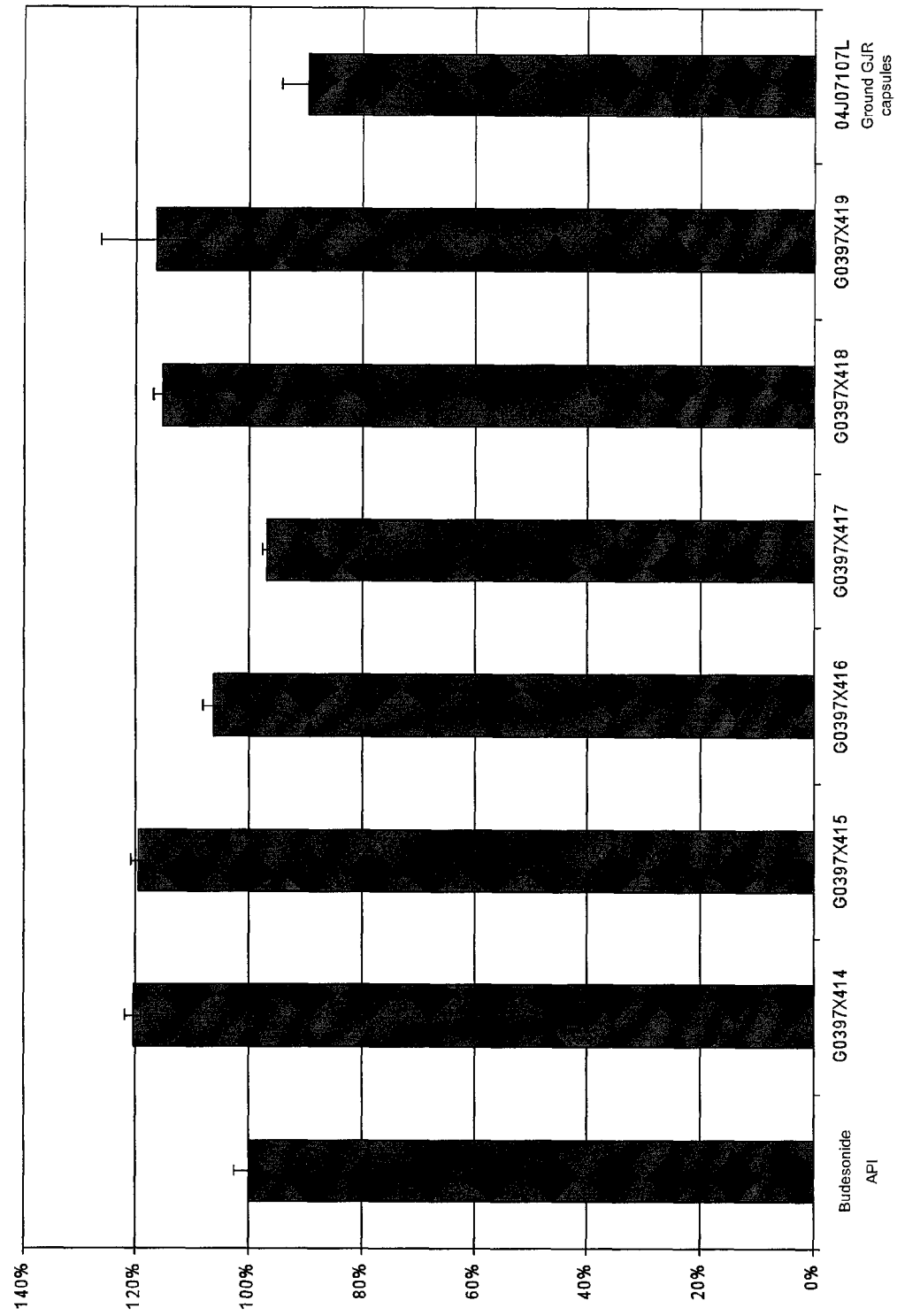
FIG. 1 shows a comparison of the quantity of budesonide released in water from different effervescent tablet formulations. Also shown is the quantity of released budesonide which can be released from gastric juice-resistant capsules, ground up by pestle and mortar, dissolved in water.

The solubility of budesonide of the individual effervescent tablets was determined in accordance with the intended manner of use by the patient. For this purpose, a respective effervescent tablet was dissolved in 10 ml of water in a suitable polypropylene measuring beaker. At the end of the effervescent reaction, the content of dissolved budesonide was determined by an HPLC method. A total of twelve determinations were made from each effervescent tablet formulation. The solubility of pure budesonide in 10 ml of water was determined simultaneously. For a better comparability, the determined water solubility of budesonide was standardised to 1.0 or 100%. In this manner, it is possible to clearly see the influence of the tested formulation ingredients on the solubility of budesonide. The solubility values obtained are shown in FIG. 1.

Compared to the solubility of pure budesonide (see FIG. 1. column "Budesonide API"), the addition of 1.4% of PVP into the effervescent tablets significantly increases the water solubility of budesonide by approximately 20% (see formulation G0397X414). If PVP is absent (see column "G0397X416") or if PVP and docusate sodium are absent (see column "G0397X417"), the quantity of released budesonide is still only within the region of the control mixture or is even lower. An addition of 2.8% or 4.8% of PVP to the effervescent tablet formulation again resulted in an increase in the quantity of released budesonide (see columns "G0397X418 and G0397X419"). Grinding and dissolving gastric juice-resistant capsules described in the prior art (FIG. 1, right-hand column) leads to poor results.

Example 2

The addition of docusate sodium further improves the usability of a mouth rinsing solution of budesonide: as a result, the hydrophobic budesonide was made more easily wettable and a greater proportion of the budesonide can dissolve (Table 2).

The intended use for the patient provides that the patient dissolves the effervescent tablet in 10 ml of water in a polypropylene measuring beaker and then uses the solution to rinse his mouth. However, this presupposes that the content of the measuring beaker can be removed approximately quantitatively and that no appreciable budesonide residues remain (Table 2).

To verify the complete removal, therefore, after an effervescent tablet had been dissolved, the mouth rinsing solution was removed and the residue of budesonide remaining in the measuring beaker was dissolved in 10 ml of methanol and determined by an HPLC method. 12 determinations were again made from each effervescent tablet formulation. Table 2 summarises the results of the experiment. In this respect, the quantity of budesonide dosage is stated which, after the mouth rinsing solution has been taken, remains adhering to the measuring beaker and is not available to the patient.

TABLE 2

Reside of budesonide remaining in the measuring beaker after application

| | Effervescent tablet (Code) | | | | | |
|---|---|---|---|---|---|---|
| | G0397X414 | G0397X416 | G0397X419 | G0397X415 | G0397X418 | G0397X417 |
| Budesonide residue in measuring beaker | 5% | 6% | 12% | 13% | 13% | 25% |

The formulations with docusate sodium clearly show the least adhesion to the measuring beaker material (see formulation codes G0397X414 and G0397X416). When this ingredient is absent from the formulation, the amount of dosage which remains as residue in the vessel during an application significantly increases.

Example 3

The effervescent tablet according to the invention was additionally optimised by the addition of N-2,3-trimethyl-2-isopropylbutanamide ("cooling agent"). The use of this auxiliary produces a cooling effect, thereby allowing an improved, more pleasant use as a mouth rinsing solution which increases the patient's adherence.

The solubility of the compositions stated in Table 1 was determined and is shown in FIG. 1. The addition of PVP and ducosate sodium increases the solubility of a budesonide effervescent tablet by approximately 20%.

The preparation of this ready-for-use mouth rinsing solution, based on a solid effervescent tablet now presents an industrially producible pharmaceutical formulation which can be dosed in a reproducible manner and is particularly suitable for use in cases of inflammation in the upper digestive tract.

Example 4

Figure 2:
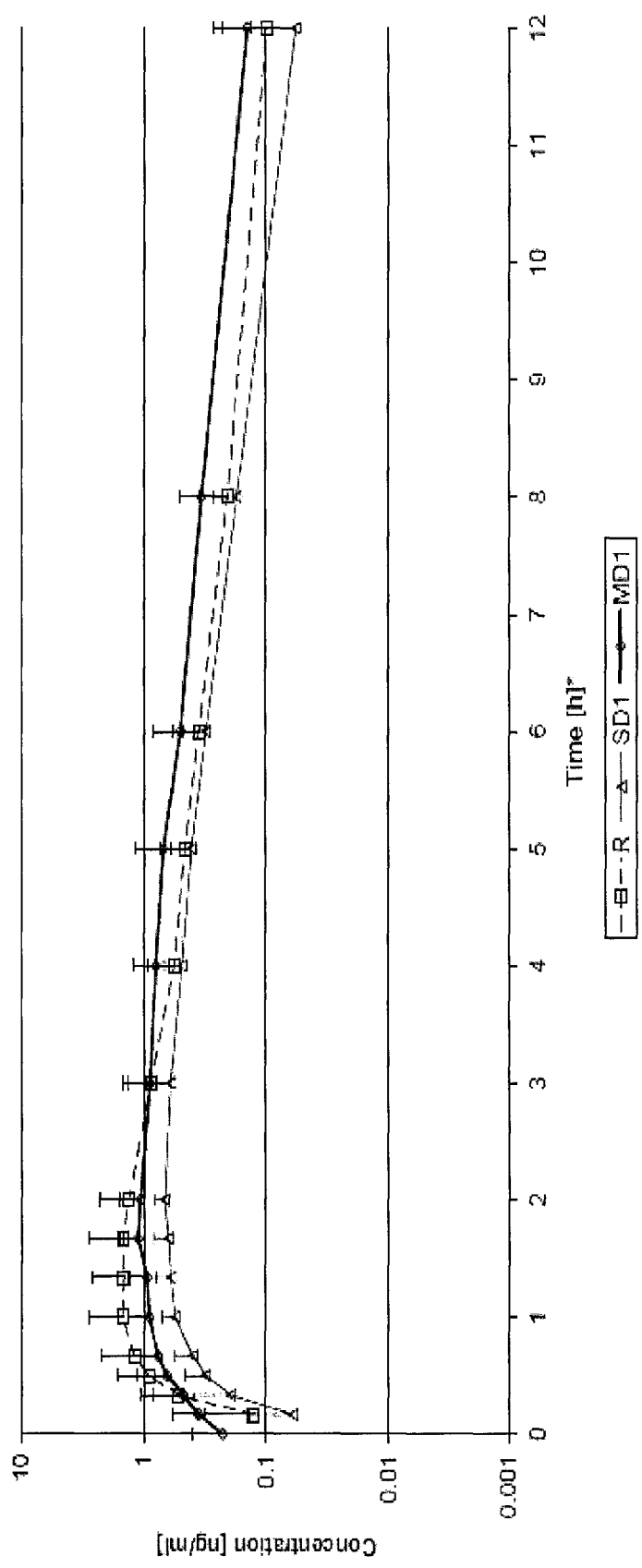
FIG. 2 shows budesonide plasma concentration time curves of 7 patients with chronically active oral graft-versus-host disease after three different treatments with budesonide:
R=per os dose of 10 ml aqueous solution with 3 mg of budesonide.
SD1=10 ml aqueous solution with 3 mg of budesonide as mouth rinsing solution for 10 minutes.
MD1=multiple dosage for 7 days of a 10 ml aqueous solution with 3 mg of budesonide, 3 times daily in a daily dose of 9 mg budesonide as a mouth rinsing solution in each case for 10 minutes. The last dose was given in the morning on the $7^{th}$ day. The curves are shown as an average ±standard deviation.

The formulation (GO397X414) prepared in this way was tested in vivo on patients with GVHD and the blood concentration was measured as an indication of the availability of budesonide in the mucosa. Surprisingly, it was found that when the selected, optimised formulation was used as a mouth rinsing solution, similarly low blood concentrations are generated as for the oral dose (per os) of the same quantity of budesonide solution (FIG. 2), although budesonide resorbed in the mouth is not subject to a first-pass effect in the liver. Since budesonide resorbed in the stomach/digestive tract is subject to a high first-pass effect in which 90% of the absorbed budesonide is metabolised, this comparable bioavailability of the mouth rinsing solution on the one hand shows an effective concentration on the mucosal layers concerned, and also a safe use which has few side effects because comparatively low blood concentrations and not relatively high blood concentrations are measured. Table 3 verifies this statement by the comparability of the pharmacological data of the formulation according to the invention with various oral forms of administration.

In a clinical pilot study, the efficacy of the formulation according to the invention was tested on 18 patients suffering from oral chronic GVHD. The objective of the open, randomised phase II study was to reduce the degree of severity of the oral chronic GVHD. After using the budesonide effervescent tablet as a mouth rinsing solution over a period of 8 weeks, it was possible to achieve an objective reduction in the degree of severity of the oral chronic GVHD, measured by the modified OMRS ("oral mucosa rating scale", according to Schubert et al., Cancer, 1992, Vol. 69, p. 2469-2477), in 11 of 18 patients (61%). As a definition of an effective response rate, only those patients were counted for whom the modified OMRS could be reduced by at least 50%, compared to the starting value. This pilot study demonstrates in an impressive manner the efficacy of the formulation according to the invention.

Table 3 shows the resorption of 3 mg of budesonide in healthy subjects and patients after a single dose. The data is stated as averages ±standard deviation or as a median with the spread in brackets.

TABLE 3

|  | $C_{max}$ (ng/mL) | $t_{max}$ (h) | $AUC_{0\text{-}tlast}$ (h*ng/mL) |
|---|---|---|---|
| 7 patients, p.o. dose of mouth rinsing solution | 1.76 ± 1.38 | 1.7 (0.5-2.0) | 5.90 ± 4.42 |
| 12 healthy subjects, p.o. dose of mouth rinsing solution | 1.23 ± 0.52 | 1.2 (0.3-1.7) | 2.67 ± 1.09 |
| 8 healthy subjects, p.o.- dose of a gastric juice-resistant capsule | 1.07 ± 0.63 | 5.0 (4.2-5.3) | 3.15 ± 2.00 |
| 7 patients, use as mouth rinsing solution | 0.77 ± 0.23 | 2.0 (1.0-3.0) | 3.61 ± 1.32 |

$C_{max}$, peak level in the plasma; $t_{max}$, time of peak level; $AUC_{0\text{-}tlast}$, area under the plasma concentration time curve up to last measurable concentration.

The invention claimed is:

1. An effervescent tablet containing budesonide, wherein said tablet contains from 0.1 to 10 mg of budesonide per effervescent tablet in combination with polyvinylpyrrolidone in a concentration of from 0.5 to 10% by weight, based on the weight of the effervescent tablet, wherein said tablet is formulated to rapidly dissolve in a specific volume of liquid so as to generate an orally-administrable mouth rinsing solution comprising a therapeutically effective amount of dissolved budesonide suitable for the treatment of inflammatory changes in the upper digestive tract.

2. The effervescent tablet according to claim 1, wherein said tablet further comprises ducosate sodium in a concentration of from 0.1% to 5.0% by weight, based on the effervescent tablet.

3. The effervescent tablet according to claim 1, wherein said tablet comprises an effervescent mixture of a pharmaceutically acceptable acid in solid form and a compound containing carbonate and/or hydrogen carbonate.

4. The effervescent tablet according to claim 1, wherein said tablet contains an agent that produces a cooling effect in the mouth, in a concentration of from 0.1 to 1.0% by weight, based on the prepared effervescent tablet.

5. A method for the treatment of inflammatory changes in the upper digestive tract, said method comprising (1) dissolving the effervescent tablet of claim 1 in a specific volume of liquid to generate a mouth rinsing solution comprising a therapeutically effective amount of dissolved budesonide and (2) orally administering said mouth rinse solution to a patient in need thereof.

6. The method according to claim 5, characterized in that the inflammatory changes of the upper digestive tract are localized in the region of the oral cavity and/or pharynx.

7. The method according to claim 5, characterized in that the inflammatory changes of the upper digestive tract are non-infectious inflammations.

8. The method according to claim 5, characterized in that the inflammatory changes of the upper digestive tract are the result of chemotherapy.

9. The method according to claim 5, characterized in that the inflammatory changes of the upper digestive tract are the result of mucositis, an autoimmune disorder of the oral cavity, Crohn's disease in the upper digestive tract or eosinophilic oesophagitis.

10. The method according to claim 5, wherein said liquid is water.

11. The method accordingly to claim 5, wherein said specific volume of liquid added is 5 to 20 ml.

12. The method according to claim 5, further comprising (3) gargling the mouth rinsing solution for a predetermined time between 2 and 15 minutes and (4) expelling said mouth rinsing solution from the mouth.

* * * * *

UNITED STATES PATENT AND TRADEMARK OFFICE
CERTIFICATE OF CORRECTION

| | |
|---|---|
| PATENT NO. | : 8,580,300 B2 |
| APPLICATION NO. | : 13/054844 |
| DATED | : November 12, 2013 |
| INVENTOR(S) | : Rudolf Wilhelm et al. |

It is certified that error appears in the above-identified patent and that said Letters Patent is hereby corrected as shown below:

In the Specification:

At column 6, line 54 (Table 2), please replace the word "Reside" with the word -- Residue --.

Signed and Sealed this
Fourth Day of March, 2014

Michelle K. Lee
*Deputy Director of the United States Patent and Trademark Office*